United States Patent

Robert et al.

[11] Patent Number: 5,298,647
[45] Date of Patent: Mar. 29, 1994

[54] AROMATIC COMPOUNDS OF AMIDE STRUCTURE DERIVED FROM AMINOBENZOIC ACIDS, HYDROXY-BENZOIC ACIDS, CINNAMIC ACIDS, UROCANIC ACIDS AND BENZIMIDAZOLES, ABSORBING UVB AND/OR UVA

[76] Inventors: Dominique Robert, 248, avenue de la Vaugine, 8300 Draguignan; Louis Jung, 205, route d'Oberhausbergen, 67200 Strasbourg, both of France

[21] Appl. No.: 123,859
[22] PCT Filed: Feb. 13, 1987
[86] PCT No.: PCT/FR87/00039
   § 371 Date: Dec. 14, 1987
   § 102(e) Date: Dec. 14, 1987
[87] PCT Pub. No.: WO87/04923
   PCT Pub. Date: Aug. 27, 1987

[30] Foreign Application Priority Data
Feb. 14, 1986 [FR] France ............... 86 02125

[51] Int. Cl.⁵ ............ C07C 321/04; C07C 229/06; C07C 229/08; C07C 229/14; C07C 233/03; C07C 233/04; C07C 233/05; C07C 233/07; C07D 233/54
[52] U.S. Cl. .......................... 560/16; 560/9; 560/15; 560/19; 560/21; 560/22; 560/23; 560/37; 560/38; 560/39; 560/41; 560/42; 560/43; 560/44; 560/45; 560/48; 560/49; 560/50; 562/426; 562/431; 562/433; 562/442; 562/443; 562/444; 562/450; 562/451; 562/452; 562/455; 564/153; 564/154; 564/155; 564/157; 564/158; 564/161; 564/162; 564/163; 564/164; 564/165; 564/167; 564/168; 564/169; 564/170; 564/171; 564/182; 564/183; 564/184; 564/185; 564/186; 564/187; 548/335.1; 548/335.5; 548/336.1; 548/338.1; 548/338.5; 548/340.1; 548/341.5; 548/342.1

[58] Field of Search ............ 560/9, 16, 15, 19, 21, 560/22, 23, 37, 38, 39, 41, 42, 43, 44, 45, 48, 49, 50; 562/426, 431, 433, 442, 443, 444, 450, 451, 452, 455; 564/153, 154, 155, 157, 158, 161, 162, 163, 164, 165, 167, 168, 169, 170, 171, 182, 183, 184, 185, 186, 187; 548/335.1, 335.5, 336.1, 338.1, 338.5, 340.1, 341.5, 342.1

[56] References Cited

FOREIGN PATENT DOCUMENTS
957162 1/1957 Fed. Rep. of Germany .
(List continued on next page.)

OTHER PUBLICATIONS
"N-Acylurocanic acid alkyl ester derivatives", *Chemical Abstracts*, 140137t, vol. 82, No. 21, May 26, 1975, by Y. Tobari et al., p. 630.
(List continued on next page.)

*Primary Examiner*—Johann Richter
*Attorney, Agent, or Firm*—Young & Thompson

[57] ABSTRACT

Aromatic compounds absorbing UVB and/or UVA, substituted with an amide function, selected from the group consisting of

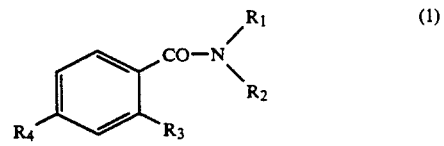

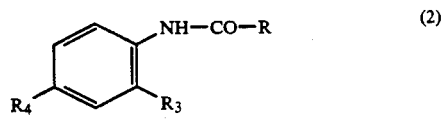

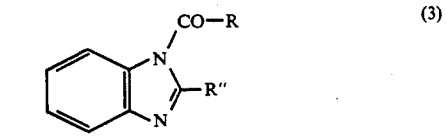

whose variable substituents are as defined in the specification, e.g.

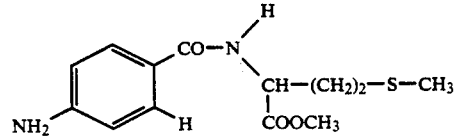

are useful as photoprotective agents or tanning accelerators.

12 Claims, No Drawings

FOREIGN PATENT DOCUMENTS

| | | |
|---|---|---|
| 1443923 | 3/1969 | Fed. Rep. of Germany . |
| 2932923 | 2/1981 | Fed. Rep. of Germany . |
| 1184710 | 7/1959 | France . |
| 890933 | 4/1964 | France . |
| 2204628 | 5/1974 | France . |
| 2579461 | 10/1986 | France . |

OTHER PUBLICATIONS

"Ultraviolet light-absorbing urocanic acid derivatives", *Chemical Abstracts*, 155513c, vol. 84, No. 22, May 31, 1976, by S. Inatsuka et al., p. 346.

"Antimalarials. Synthesis and Antimalarial Activity of 1-(4-Methoxycinnamoyl)-4-(5-phenyl-4-oxo-2-oxazolin-2-yl) piperazine and Derivatives", *Journal of Medicinal Chemistry*, vol. 18, No. 12, 1975, by T. Herrin et al. pp. 1216-1223.

"Melt Spinning of Syndiotactic 1,2-Polybutadiene for Preparation of Carbon Fibers", *Journal of Polymer Science*, vol. 21, 1983, by H. Ashitaka et al., pp. 1111-1124. *Chemical Abstracts*, vol. 101, No. 14, Oct. 1, 1984, 112584d, p. 85. (Copy not available).

"Isolation and synthesis of trans- and cis-(−)-clovamides and their deoxy analogs from the bark of Dalbergia melanoxylon", *Chemical Abstracts*, vol. 94, No. 19, May 11, 1981, 157211h, by F. Van Heerden et al., p. 692.

"Putrescine amides from Kniphofia species", *Chemical Abstracts*, 109444f, vol. 73, No. 20, Nov. 16, 1970, by H. Ripperger et al., p. 340.

"Corrosion inhibitor", *Chemical Abstracts*, 76372b, vol. 90, No. 10, Mar. 5, 1979, by S. Yamanaka et al., p. 269.

"Substantivity of sunscreens: an appraisal of some quaternary ammonium sunscreens", *Chemical Abstracts*, 102334r, vol. 105, No. 12, Sep. 22, 1986, by M. Saettone et al., p. 314.

"Preparation, properties, and reactions of some conjugated heteroenoid compounds and related compounds", *Chemical Abstracts*, 46109a, vol. 85, No. 7, Aug. 16, 1976, by H. Holmes et al., p. 486.

"Stabilization of aseobic acid and related compounds by urocanates", *Chemical Abstracts*, 116079c, vol. 82, No. 18, May 5, 1975, by K. Hasunuma, p. 287.

"Benziminazoles related to Pteroic and Pteroylglutamic Acids", *Chemical Society*, 1949, by F. King et al., pp. 1401-1406.

"Isolation of urocanylglycine, a urinary derivative of histidine", *Chemical Abstracts*, vol. 73, No. 19, Nov. 1970, No. 96092n, by J. Pousset et al., p. 139.

"Antisunburn agents", *Chemical Abstracts*, vol. 59, No. 7, Sep. 1963, Col. 7316h-7317a, by R. Masuda et al.

"Synthesis and antiinflammatory activity of some salicylic acid amides—derivatives of alpha-amino acids", *Chemical Abstracts*, vol. 90, No. 7, Feb. 1979, No. 55256b, by N. Divanyan et al., p. 641.

*The Merck Index*—An Encyclopedia of Chemicals and Drugs, 9th Edition, 1976, Editor Martha Windholz et al., Merck & Co., Inc., No. 430, p. 58.

Ibid No. 449, p. 61 (1976).

"Prodotti Di Una Reazione Tra 1H-Indazol-3-Olo E Cloroacetato di Etile", *Il Farmaco Ed. Sc.*, vol. 32, No. 7, by M. Bonanomi et al., pp. 490-501.

"Probiotics: Antistaphylococcal Activity of 4-Aminocyclohexane-carboxylic Acid, Aminobenzoic, and their Derivatives and Structure-Activity Relationships", vol. 66, No. 6, Jun. 1977, by A. Fujii, pp. 844-848.

AROMATIC COMPOUNDS OF AMIDE STRUCTURE DERIVED FROM AMINOBENZOIC ACIDS, HYDROXY-BENZOIC ACIDS, CINNAMIC ACIDS, UROCANIC ACIDS AND BENZIMIDAZOLES, ABSORBING UVB AND/OR UVA

The present invention has for an object the synthesis and/or use of compounds capable of opposing, in the form of solar filters and if desired by induction of melanogenesis, the harmful effects of solar radiation and photosensibilization reactions induced in man, especially during use of certain medicaments or perfumes or cosmetic preparations. They are aromatic compounds absorbing UVB and/or UVA, substituted with an amide function, as well as derivative compounds obtained by introduction of an ethylenic spacer between the aromatic structure and the amide function, without modification of the spectral characteristics.

At present, a wide range of sun-blocking preparations have been developed for protecting the skin. These preparations contain as active ingredients compounds capable of selectively absorbing harmful solar radiation. But these products have the disadvantage of being difficult to apply to the surface of the skin, and of being eliminated during their use (by sweat, swimming in the ocean, . . . ) Moreover, certain among them pass through the skin and into the blood stream (D. Claus - Doctorate thesis from the University of Strasbourg, mentioned in *Pharmacie* 1982); they thus lose their activity and risk endangering the health of the user in case of prolonged use. Derivatives of para-methoxycinnamic acid are the most widely used sun screens in the world. To retain this type of compound on the surface of the skin, one solution consists of attaching to their chemical structure isolated amino groups (French patent No. 81.08429), or amino acids or peptides which bind to the surface of the skin. Thus, two series of amino acid compounds of para-methoxycinnamic acid and trans-urocanic acid have recently been synthesized, and their sun-blocking properties claimed (French patent No. 84.100009 and French patent No. 85.04898). For protecting against harmful solar radiation, another solution consists of stimulating the principal natural protective system of the skin, melanogenesis. At the present time, none of the products used as sunscreens claim that property.

The new compounds according to the invention have either or both of the two properties necessary to obtain maximum effectiveness in solar protection, namely prolonged absorption of harmful ultraviolet radiation by improved skin adherence of the compound, and induction of melanogenesis. The chemical structures envisioned must be able to be solubilized either in a non-aqueous or aqueous solvent; an amphoteric character will permit a disposition at the interface of the globules of an emulsion. The same compound having one or both of the photoprotective properties described above will thus exist either in the form of a liposoluble ester or will have a free carboxylic group, either in the form of an aminoalkyl chain ester, or in a hydrosoluble aminoaryl chain ester, hydrochlorides being an example of hydrosoluble amine salts, or in the form of hydrosoluble organic or inorganic salts of the free carboxylic groups. The ester function may be replaced by an amide function. All the compounds according to the invention are capable of absorbing ultraviolet radiation between 360 nm and 260 nm with a maximum which may be situated either in UVA or UVB, or conjointly in UVA and UVB. The original compounds described for the first time and for which the present invention is claimed are aromatic compounds absorbing UVB and/or UVA, substituted with an amide function, characterized in that they respond to the formulas 1 to 3,

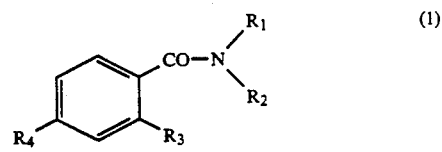

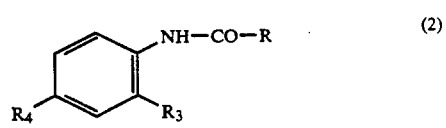

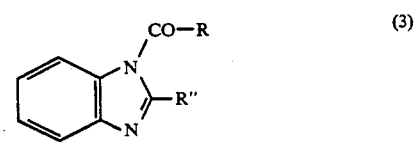

and in that, by introduction of an ethylenic spacer between the aromatic structure and the amide function without modification of the spectral characteristics, derivative compounds of formula 4 are obtained

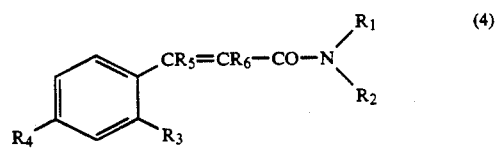

wherein $R_1$ may be hydrogen, alkyl or aryl $R_2$ may be a substituent of the formula:

in which X and Y may be hydrogen, alkyl, aryl, aminoalkyl or aminoaryl; or

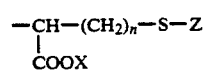

in which Z may be hydrogen, alkyl, aryl, aminoalkyl or aminoaryl, X may be hydrogen, alkyl, aryl, aminoalkyl or aminoaryl and n may be an integer from 1 to 6, preferably 1 or 2

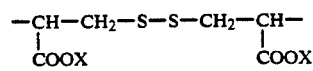

on which are fixed two chromophore-filtering molecules of the structure 1 to 4, wherein X may be hydrogen, alkyl, aryl, aminoalkyl or aminoaryl, or exist in the form of an organic or inorganic salt.

$R_1$ may also be equal to $R_2$.

may be urocanic acid or a derivative of urocanic acid of one of the following four types:

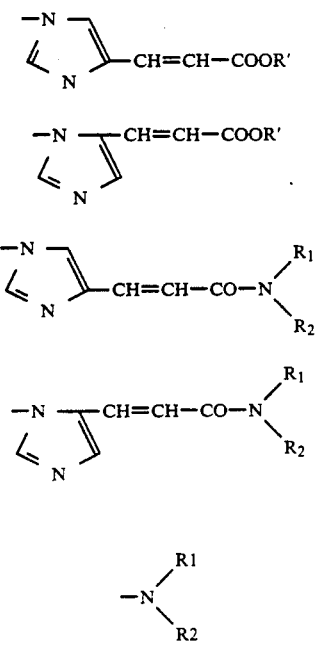

may be a peptide structure comprising two or more amino acids of which the terminal or branched amino or acid functions may be free or associated in ester or amide groups.

R3 and R4 may be hydrogen, an alkoxy group of the type CH$_3$—O— a hydroxy group, an acid group, a primary amino group, a —NH—COR amide group, or an ester group of the type —COOR'. R3 and R4 may be identical or different. R may be:

$$-\text{CH}-Y, \text{ or}$$
$$\phantom{-\text{CH}-}\text{NH}-X$$

$$-\text{CH}-(\text{CH}_2)_n-\text{S}-Z,$$
$$\phantom{-\text{CH}-}\text{NH}-X$$

$$-\text{CH}-\text{CH}_2-\text{S}-\text{S}-\text{CH}_2-\text{CH}-$$
$$\phantom{-\text{CH}-}\text{NH}-X \phantom{-\text{CH}_2-\text{S}-\text{S}-\text{CH}_2-} \text{NH}-X$$

in which Z may be hydrogen, alkyl or aryl, n is an integer from 1 to 6, preferably 1 or 2 and X and Y may be hydrogen, optionally hydroxylated branched or straight chain alkyl, aryl, aminoalkyl or aminoaryl. R' may be hydrogen, alkyl, aryl, aminoalkyl, aminoaryl, or an organic or inorganic salt thereof. R" may be alkyl, aryl, aminoalkyl or aminoaryl. R5 and R6 may be hydrogen, alkyl or aryl. R5 and R6 may be identical or different.

For the structure 4, the following derivatives are excluded:

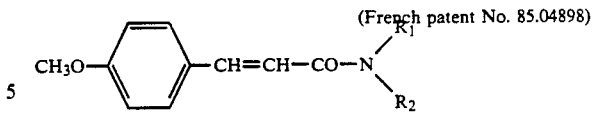

(French patent No. 85.04898)

In the present specification, the term "alkyl" designates straight or branched chain aliphatic hydrocarbon groups containing 1 to 12 carbon atoms. Lower alkyl is preferred, namely alkyl groups containing 1 to 4 carbon atoms. The term "alkyl" may also designate hydroxyalkyl.

The term "aryl" designates non-heterocyclic aromatic groups of the phenyl, phenol and benzyl type, as well as higher homologs, substituted or unsubstituted, as well as heterocyclic aromatic groups having 2 to 7 carbon atoms in the aromatic portion, and 1 to 4 heteroatoms which may be oxygen, nitrogen and sulfur, such as furan, pyridine and oxazole.

The term "aminoalkyl" designates aliphatic hydrocarbon groups containing 1 to 12 carbon atoms and 1 to 3 nitrogen atoms, straight or branched chain. Groups containing 1 to 4 carbon atoms and 1 nitrogen atom are preferred.

The term "aminoaryl" designates nitrogenized cyclic aromatics.

The term "inorganic salt" preferably designates a salt of sodium, potassium or calcium.

The term "organic salt" preferably designates a salt obtained by the action of a primary, secondary or tertiary amine on the carboxylic group; a salt of ethanolamine, piperidine, pyrolidine, pyridine or their derivatives is preferred.

Among these general structures, are claimed especially the amides due to combination between anthranilic acid, para-aminobenzoic acid, salicyclic acid or 2-cyano-3-phenylcinnamic acid and amino acids or peptides devoid of sulfur such as tyrosine, histidine, glutamic acid, pyroglutamic acid or sulfur-containing peptides or amino acids such as methionine, cysteine, S-methylcysteine, S-benzylcysteine, cystine, glutathione, and oxidized glutathione.

Among these claimed compounds are found compounds responding to the formulas 1a, 1b, 1c,4a, 4b and 4b', which are due to the combination between anthranilic acid, para-aminobenzoic acid, salicyclic acid, 2-cyano-3-phenylcinnamic acid or para-methoxycinnamic acid, and an amine function of an amino acid or peptide.

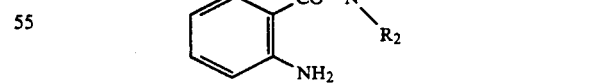 (1a)

with the exclusion of the methyl ester derivative of glycine, R1=H and R2=CH2—COOCH$_3$ (Spath, Kuffner, B. 1934, 67, 494) and with the exclusion of the derivative of DL alanine, R1=H and

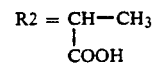

(Colles, Gibson, Soc. 1931 279,282).

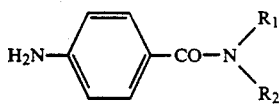 (1b)

with the exclusion of the derivatives where

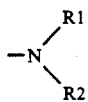

corresponds to the structure —NH—CH$_2$—COX' of glycine or to a structure

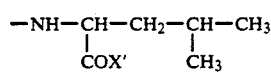

of leucine, X' corresponding to hydroxy or to a peptide structure. (Landsteiner, Van der Scheer, J. Exp. Med. 1939, 69, 705 et seq. and ibid 1934, 59, 769 et seq. and ibid 1932, 55, 781 et seq. Resume Beilstein ed. Berlin, Amino-derivate der' Monocarbonsauren, E III 14, p. 1070 and 1071) and with the exclusion of the derivative of DL alanine, R1=H and R2=—CH(COOH)—CH$_3$ and derivatives where DL alanine is replaced either by DL valine, or by DL isoleucine, or by DL serine, or by DL methionine, or by aspartic acid. (Beilstein, ed. Berlin, Amino-derivate der Monocarbonsauren, EIII, 14 p. 1071 and 1073.)

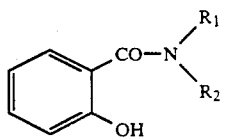 (1c)

with the exclusion of the derivatives where

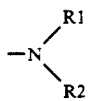

corresponds to a structure —NH—CH$_2$—COOX with either X=H (glycine derivative), or X=C$_2$H$_5$ (ethyl ester derivative of glycine) (Butler, Harington, Yu 1, Biochem. J. 1940, 34, 833–840).
and with the exclusion of the derivatives where: R1=H and

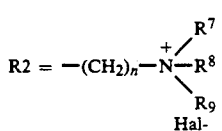

(U.S. Pat. No. 3,506,758) R1=H and R2=—C$_6$H$_5$ (U.S. Pat. No. 2,874,090) Hal$^-$ designates a halogen atom, Cl$^-$,Br$^-$ R7 designates an alkyl group having 1 to 5 carbon atoms, R8 designates an alkyl group having 1 to 5 carbon atoms. R9 designates an alkyl group or a benzylalkyl group having 3 to 18 carbon atoms. n is an integer from 2 to 12.

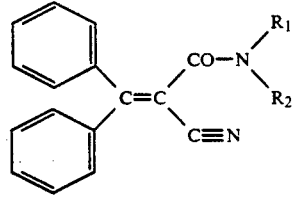 (4a)

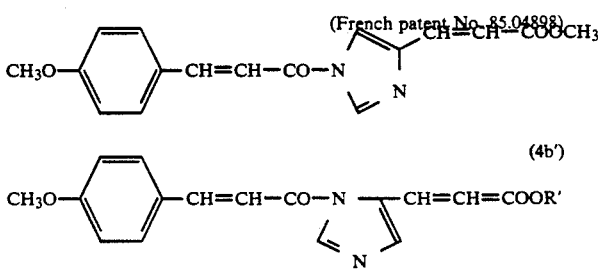

with the exclusion of the following derivative

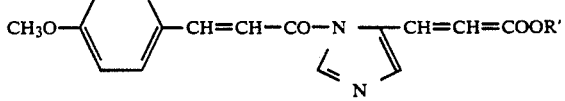

(French patent No. 85.04898)

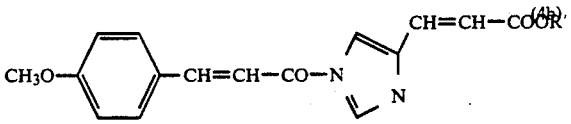 (4b')

where R' may exist in the form of a mineral or organic salt R1 and R2 have the same meaning as in the general structures 1 to 4.

These structures, which thus correspond to a chromophore coupled to an amide structure of which the amine is of amino acid or peptide origin, permit excellent fixation to the skin, especially at the level of the epidermis. This is especially true when the bound amino acid or peptide also has sulfur groups.

Also especially claimed are the products responding to the formulas 2a, 2b and 3a characterized in that they have a chromophore coupled to an amide structure of which the carbonyl component is of amino acid or peptide origin. These structures permit excellent fixation to the skin, particularly at the level of the epidermis, for example with pyroglutamic acid. This is also particularly the case when the bound amino acid or peptide also contains sulfur groupings.

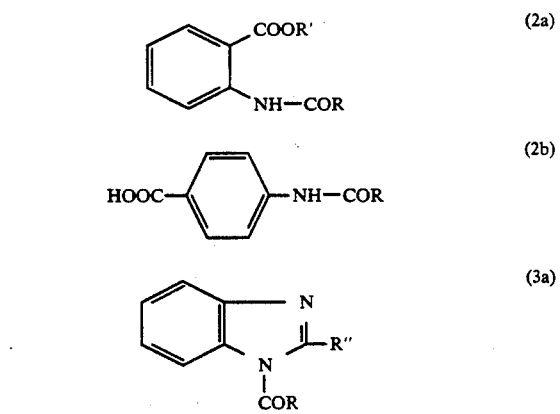

wherein R, R' and R" have the same definitions as in the general structures 1 to 4.

Finally, especially claimed are the products corresponding to the formulas 1d and 1e, characterized in that they have a double amide structure of anthranilic acid or para-aminobenzoic acid.

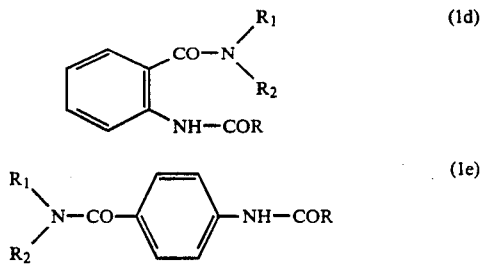

and the products due to combination between para-methoxycinnamic acid and urocanic acid or one of its derivatives of the following two forms:

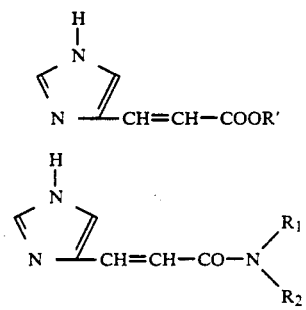

where R' and

have the same meaning as in claim 1. Urocanic acid and its derivatives may be present in the cis or trans form. These latter products have two coupled chromophore groups that may have hydrosoluble properties. All these structures may contain aminoalkyl or aminoaryl groups in the form of salts, for example hydrochlorides or organic or mineral salts of the free carboxylic group, which adds a fourth water soluble property, the other compounds being rather liposoluble. R1, R2, R and R' have the same meaning as in the general structures 1 to 4.

The invention also has as an object a process for preparing derivatives as defined in formulas 1 to 4 above.

Generally the synthesis processes consist of:

1) preparing acid chloride by reacting, for example, thionyl chloride with acid in an organic solvent.

2) reacting the preceding acid chloride with a compound having a primary or secondary amino group in an organic solvent, in the presence of triethylamine.

3) optionally salifying with a mineral or organic alkaline agent, the compound having a free carboxylic group.

4) optionally salifying with an organic base a primary or secondary or tertiary amino group.

It will especially be a matter of reacting anthranilic acid chloride or para-aminobenzoic acid chloride or salicyclic acid chloride or 2-cyano-3-phenolcinnamic acid chloride, with an amino function of a sulfur-containing or sulfur-devoid amino acid or peptide. For certain compounds, the step of forming acid chloride is not necessary. The peptidic bond may be obtained by combination with the carboxylic function and the amine function in the presence of dicyclohexylcarbodiimide or a similar reagent used in peptide synthesis. To obtain compounds of the formulas (4b) and (4b'), the synthesis process consists of reacting para-methoxycinnamic acid chloride with the amine function of urocanic acid or one of its derivatives, of one of the two following forms:

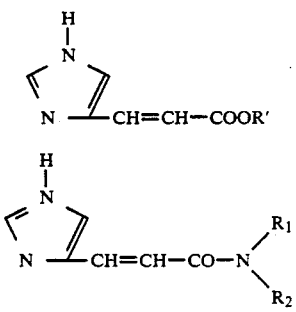

where R' and

have the same definition as in claim 1.

All the compounds of the general formulas 1 to 4, without exception, as well as the compounds of which the chemical structure and the sun-blocking properties have already been described and claimed in French patents Nos. 84.10009 and 85.04898 are capable of inducing melanogenesis to a greater or lesser extent according to the structure of the molecule. This is especially the case for formulas of the structures 4c and 5. The property of inducing melanogenesis is claimed for all the compounds of formulas 1 to 5 described.

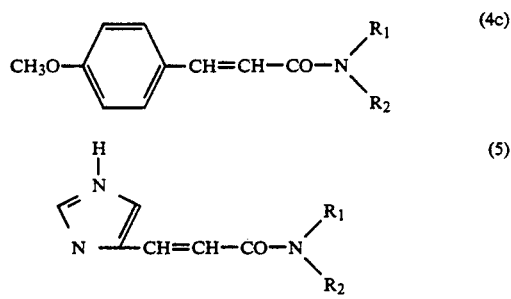

wherein R1 and R2 may be hydrogen, alkyl, aryl, aminoalkyl, aminoaryl, and advantageously they may have the same definition as in claim 1. R1 and R2 may be identical or different.

All the compounds of general formulas 1 to 4, without exception, are also solar filters, characterized in that they selectively absorb UVB and/or UVA radiation and they are fixed at the level of the keratins for the derivatives of cysteine, cystine, methionine and other sulfur-containing amino acids and peptides. They may induce melanogenesis, and thus perform a triple role, namely selectively filtering UVB and/or UVA radiations, being fixed at the level of the epidermis of the skin and more or less significantly increasing the quantity of melanins, substances basic to the principal natural system of anti-solar protection. This is especially the case for derivatives of trans-urocanic acid, para-aminobenzoic acid and para-methoxycinnamic acid, where a strong induction of melanogenesis was observed. The filters which comprise an amide structure of amino acid or peptidic origin thus possess a very substantial character which assures in addition to development of natural protection, namely induction of melanogenesis, excellent artificial photoprotection for the duration of topical application. The products described are particularly adapted for topical usage given that, as mentioned above, only a portion of their structure is derived from natural substances ordinarily present in the epidermis, and that they thus have a perfect innocuity and tolerance. The most frequently employed amino acids and peptides are:

glutamic acid, pyroglutamic acid, aromatic amino acids, especially tyrosine and histidine, sulfur-containing amino acids, especially methionine, cysteine, S-methylcysteine, S-benzylcysteine, cystine, glutathione, oxidized glutathione, photoprotective amino acids, especially urocanic acid. These examples are not to be construed as limiting.

Owing to their properties, the compounds according to the invention could thus be used in different fields. In cosmetology, the compounds of formulas 1 to 4 could be used:

1) As solar filters when they have good spectral absorption, as well as a marked substantive character due to their structure that permits assuring their functions throughout their retention at the level of the skin.

2) As tanning accelerators by inducing melanogenesis, a property that we claim for all the products described herein, comprising among them urocanic acid. Depending on their chemical structure, induction of melanogenesis is more or less pronounced. In certain cases, in particular during tanning research, powerful inducers will be preferred. In other cases, especially for localized applications, higher concentrations of less powerful inducers will be preferred so as to be able to take advantage of the filtering power and the property of fixation to the keratins and tissues of the skin.

These products could also be used in the perfume industry, or in cosmetic preparations, especially those containing perfumes based on essence of bergamot. The increase in the production of melanins associated with the solar filtering properties, are opposed to the photosensibilization reactions arising from the UVA-bergaptene synergy that causes spotted pigmentary dermatitis-type photodermatosis. In that case, two types of uses are contemplated:

In the case of use of the compound solely as a solar filter, a concentration of the order of 0.1 to 5% of the preparation will be chosen, so as to prevent formation of photodermatoses. In case of using a compound that acts both as a solar filter and an inducer of melanogenesis, concentrations on the order of 1 to 10% will be chosen. The local pigmentation observed is due to melanins of which the cutaneous presence will diminish when application is halted.

Finally, the actual development of photodermatoses due to medicaments or any other photosensibilizing product thus leads to envision the use by topical pathways of these products in the pharmaceutical industry. A higher concentration of melanins at the level of the skin, and in the presence of a substance fixed to the keratins preventing interaction of solar radiation, will permit safely using as medicament certain molecules responsible for photodermatosis. Among the medicaments inducing photosensibilization reactions, may be mentioned contact photosensibilizing agents such as:

salicylanilides and their derivatives sulfonamides and their derivatives phenothiazines pigments and colorants such as Bengal rose coal tar and certain of its derivatives and various products such as quinine, tretinoine, benzoylperoxide, etc . . . and active principles administered by general routes at the onset of photodermatosis, such as:

psoralenes tetracyclines sulfonamides sulfonylureas such as tolbutamide thiazides and diuretic sulfamides nalidixic acid tricyclic antidepressors such as amitriptyline and various compounds such as amiodarone, griseofulvin, quinidine, methotrexate, dicarbazine, fluorouracile and vinblastine. This list is not to be construed as limiting.

So as to demonstrate the inductive activity of various products in the synthesis of melanins, two types of experiments were conducted: first, an entire dosage of melanins extracted from cultured melanomic cells, second, a dosage of the precursors of melanins, especially dopa and 5 S-cysteinyldopa. The IGR 37 cellular strain used was produced at the Gustave Roussy Institute from a human metastasic tumor. It is cultivated in minimum essential medium (MEM) supplemented with 2 mM glutamine, 9 $\mu$M proline, 25 $\mu$M vitamin C and 5% fetal calf serum. The medium is renewed twice per week and the cultures are transplanted once per week in culture flasks having a surface of 175 cm$^2$. The cultures are maintained at 37° C. in a humid atmosphere with a $CO_2$ content of 5%.

For the total dosage of melanins, we proceeded in the following manner: the first day, a million cells were introduced in culture flasks containing the previously-described medium. The second day, the first medium is replaced by medium containing products according to the invention (MEM+ medium). The fourth day, the cells are separated with a trypsine solution and counted with a haemocytometer. The cells are then centrifuged at 3,000 rpm for 10 mins.; the supernatant is decanted and the cellular underflow is stored at −20° C. Prior to their incorporation in the medium, the products according to the invention are dissolved in DMSO. The solutions are sterilely filtered on filters having pore sizes of 0.22$\mu$m. The active concentrations retained are of the order of 0.01 mM. Each DMSO solution in the medium is present therein at a maximum concentration of 0.1%.

Each experiment is carried out using a minimum of 4 flasks. A minimum of 4 control flasks is cultivated in the same conditions in the presence of 0.1% DMSO. All the operations are effected in the absence of ultraviolet radiation; the flasks and especially the solutions are protected with aluminum foil. The dosage is realized according to the method of WHITTAKER "changes in melanogenesis in cell culture" [Dev. Biol. 8, 99-127 (1963)]. The cellular underflows are extracted three times with 5% trichloroacetic acid at 4° C., two times with a (1:3) ether-ethanol mixture at 4° C. and once with absolute ether at ambient temperature. After drying, the residue is dissolved in 0.85M soda and heated for 10 mins. at 100° C. After cooling, the optical density is measured at 400 nm with a UV/visible spectrophotometer. The melanin content is expressed in terms of optical density per cell.

Results: addition of the products according to the invention in the culture medium provokes an increase in the optical density on the order of 30 to 70% relative to the flasks of cellular cultures that were not treated.

For the second study corresponding to the dosage of melanin precursors, the melanomic cells are cultivated in the same manner as in the preceding study. The cellular underflows are then dissolved in 4N perchloric acid and centrifuged at 48,000 g for 15 mins. at 4° C. The supernatants are directly recovered in centrifuge tubes containing a pH 4 mixture of alumina and sodium ethylenediaminetetraacetate. Each tube is then adjusted to pH 8.6 (±0.01) with 5N soda. After 15 mins. of agitation, the tubes are centrifuged at 5,600 rpm for 5 mins. at 4° C. The supernatant is discarded and the alumina-sodium ethylenediaminetetraacetate mixture is washed with a pH 8.6 phosphate buffer. The operation is repeated twice. After the second centrifugation, the alumina-sodium ethylenediaminetetraacetate mixture is eluted with 0.5N perchloric acid and agitated for 15 mins. The tubes are then centrifuged at 4,600 rpm for 5 mins. at 4° C. The supernatant is removed and filtered. Dosage is effected immediately, or the supernatant is frozen in a hemolysis tube for later dosage. The dosage is made with HPLC on a 254 nm UV/visible detecting apparatus. The column employed is of the 3 µm ODS ultraphere type (4.6 mm × 7.5 cm). The mobile phase is constituted of 95% 3 mmoles orthophosphoric acid/1 water
5% $CH_3OH$ The melanin precursors prepared dopa and 5-S-cysteinyl-dopa (5-SCD). 200 ng/ml control solutions are effected with dopa and 5-S-cysteinyldopa. Dopa and 5-SCD have respective retention times of 2 mins. and 4 mins. 30.

Results: The cells contacted with the product according to the invention have an overall dopa and 5-SCD content greater by about 40% in the described experimental conditions.

Finally, in man, the application of a dermo-pharmaceutical composition containing one of these products provokes a visible acceleration in tanning relative to untreated areas, after 6 to 8 days. This dermo-pharmaceutical composition combines the product with an appropriate solution, emulsion or spray carrier, and is applied to the surface of the skin.

The preparation of two of the new compounds is set forth hereinafter, by way of non-limiting example.

EXAMPLE I

Synthesis of N(4-aminobenzoyl)-L-methionine

In an Erlenmeyer flask, 1.35 g of para-aminobenzoic acid chloride are dissolved in 20 ml benzene in the presence of 2.8 ml triethylamine. 1.49 g L-methionine is added progressively and the resultant mixture is filtered. After evaporation of the filtrate to dryness under vacuum (15 mm Hg), the residue is dissolved in N hydrochloric acid and extracted with chloroform. The chloroformic solution is successively washed with several ml of 10% aqueous $HKCO_3$ solution and with water. It is then collected, dried over magnesium sulfate and evaporated. The product obtained is precipitated in cyclohexane and filtered. After recrystallization in a (1:1) mixture of 95 alcohol-water, 1.95 g of white crystals are isolated. M.p.: 172° C.

EXAMPLE II

Synthesis of Methyl N,N'-bis[3-[1-(4-methoxycinnamoyl)-4-imidazoyl]-2-propene-oyl] L cystine dicarboxylate

First Step

Synthesis of methyl N,N'-bis[3-(4-imidazoyl)-2-propene-oyl] L-cystine dicarboxylate In an Erlenmeyer flask, 1.38 g 3-(1H-4-imidazoyl)-2-propenoic acid, 2.06 g dicyclocarbodiimide (DCC), 1.705 g L cystine methyldiester and 10 ml triethylamine are agitated in 50 ml of a 50/50 acetonitrile-tetrahydrofuran mixture for 3 hours. The obtained dicyclohexylurea precipitate is eliminated by filtration, and the filtrate is evaporated with the aid of a rotary evaporator. The residue is dissolved in N hydrochloric acid, and extracted with chloroform. The chloroformic solution is then washed with several ml of a 10% aqueous $HKCO_3$ solution. It is then collected, dried over magnesium sulfate and evaporated. The product obtained is precipitated in cyclohexane and filtered.

Second Step

In an Erlenmeyer flask, 1.016 g of the amide obtained during the first step and 1 ml triethylamine are mixed in 20 ml anhydrous benzene. 784 mg para-methoxycinnamic acid chloride is added. After several minutes of agitation, the solution is filtered and evaporated with the aid of a rotary evaporator. The residue is dissolved in N hydrochloric acid and extracted with chloroform. The chloroformic solution is then washed with several ml of a 10% aqueous $HKCO_3$ solution. It is then collected, dried over magnesium sulfate and evaporated. The product obtained is precipitated in cyclohexane and filtered. After recrystallization in a 95% ethanol-water mixture (1:1), yellow crystals are isolated. M.p.: 140° C.

We claim:

1. A compound of the formula selected from the group consisting of

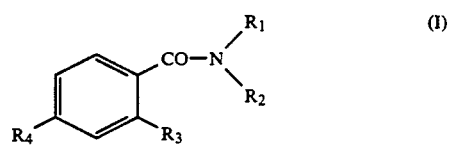

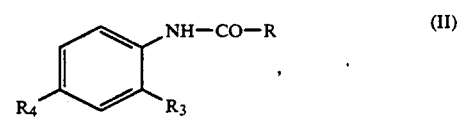

and

-continued

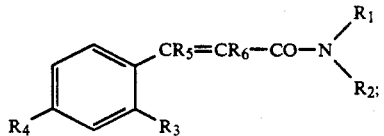

wherein R is a member selected from the group consisting of

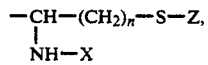

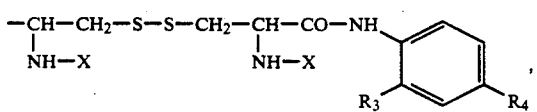

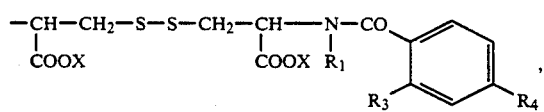

and

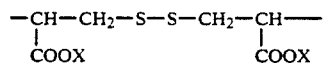

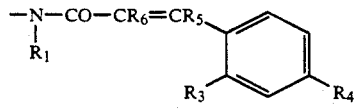

$R_1$ is hydrogen, alkyl or aryl;
$R_2$ is hydrogen, alkyl, aryl, or a member selected from the group consisting of

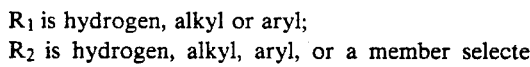

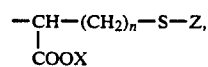

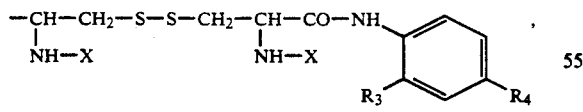

and

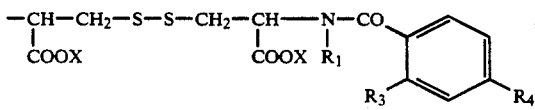

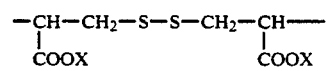

-continued

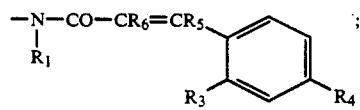

$R_3$ and $R_4$ are each independently selected from the group consisting of hydrogen, hydroxy, $CH_3$—O—, an acid group, primary amino, —NH-COR, and —COOR'; and $R_5$ and $R_6$ are each independently selected from the group consisting of hydrogen, alkyl, cyano and aryl;

or wherein

of Formulas (I) and (III) above is a member selected from the group consisting of

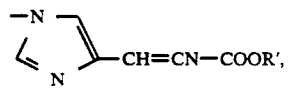

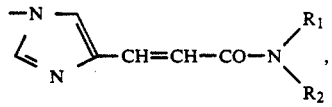

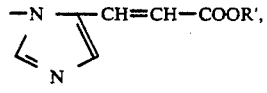

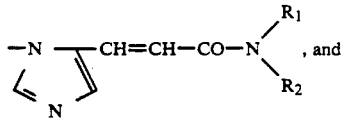

, and a peptide structure comprising at least two amino acid residues;

in which X and Y are each independently selected from the group consisting of hydrogen, alkyl, hydroxyalkyl, aryl, aminoalkyl and aminoaryl; Z is hydrogen, alkyl or aryl; n is an integer from 1 to 6; and R' is selected from the group consisting of hydrogen, alkyl, aryl, aminoalkyl, aminoaryl, and an organic or mineral salt;

excluding compounds of the formula (I) wherein $R_4$ is H, $R_3$ is $NH_2$, $R_1$ is H and $R_2$ is —$CH_2$—$COOCH_3$; wherein $R_4$ is H, $R_3$ is $NH_2$, $R_1$ is H and $R_2$ is

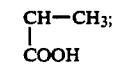

wherein $R_4$ is $NH_2$, $R_3$ is H, $R_1$ is H, and $R_2$ is —$CH_2COX'$ or

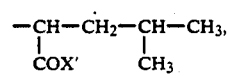

in which X' is hydrogen or a peptide residue; wherein $R_4$ is H, $R_3$ is $NH_2$, $R_1$ is H and $R_2$ is —CH(COOH)—CH$_3$, —CH(COOH)—CH(CH$_3$)$_2$, —CH(COOH)—CH$_2$CH(CH$_3$)$_2$, —CH(COOH)—CH$_2$OH, —CH(COOH)—(CH$_2$)$_2$—S—CH$_3$, or —CH(COOH)—CH$_2$COOH; wherein $R_4$ is H, $R_3$ is OH, $R_1$ is H and $R_2$ is —CH$_2$COOX,

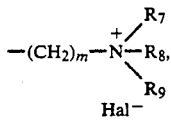

or —C$_6$H$_5$ in which Hal$^-$ is Cl or Br, $R_7$ and $R_8$ are C$_{1-5}$alkyl, $R_9$ is C$_{3-8}$alkyl or benzylalkyl, and m is an integer from 2 to 12;

and excluding compounds of the formula (III) wherein $R_4$ is —OCH$_3$ and $R_3$, $R_5$ and $R_6$ are H.

2. A compound according to Formula (I) of claim 1, wherein $R_4$ is H and $R_3$ is $NH_2$.

3. A compound of Formula (I) according to claim 1, wherein $R_4$ is $NH_2$ and $R_3$ is H.

4. A compound of Formula (I) according to claim 1, wherein $R_4$ is H and $R_3$ is OH.

5. A compound of Formula (III) according to claim 1, wherein $R_3$ and $R_4$ are H, $R_5$ is phenyl, and $R_6$ is —CN.

6. A compound according to Formula (III) of claim 1, wherein $R_3$, $R_5$ and $R_6$ are H, $R_4$ is —OCH$_3$, and wherein

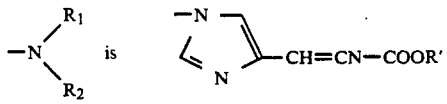

7. A compound of Formula (II) according to claim 1, wherein $R_4$ is H and $R_3$ is COOR'.

8. A compound of Formula (II) according to claim 1, wherein $R_4$ is COOH and $R_3$ is H.

9. A compound of Formula (I) according to claim 1, wherein $R_4$ is H and $R_3$ is NHCOR.

10. A compound of Formula (I) according to claim 1, wherein $R_3$ is H and $R_4$ is NHCOR.

11. A compound of Formula (III) according to claim 1, wherein $R_4$ is —OCH$_3$, $R_3$, $R_5$ and $R_6$ are H, and wherein

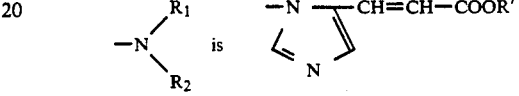

12. An aromatic compound as claimed in claim 1, which is

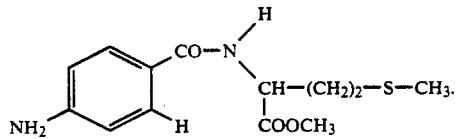

* * * * *